US012005070B2

(12) United States Patent
Aizawa et al.

(10) Patent No.: US 12,005,070 B2
(45) Date of Patent: Jun. 11, 2024

(54) PROTECTIVE AGENT FOR KERATOCONJUNCTIVA OR SUPPRESSIVE AGENT FOR KERATOCONJUNCTIVAL DISORDER

(71) Applicants: TOYO SUGAR REFINING CO., LTD., Tokyo (JP); OTSUKA PHARMACEUTICAL FACTORY, INC., Tokushima (JP)

(72) Inventors: Kyo Aizawa, Chiba (JP); Yoshihisa Iida, Tokyo (JP); Takashi Shimoida, Tokyo (JP); Yasuhiro Kotani, Tokyo (JP); Koushi Iwata, Tokushima (JP); Kazuhisa Doi, Tokushima (JP)

(73) Assignees: TOYO SUGAR REFINING CO., LTD., Tokyo (JP); OTSUKA PHARMACEUTICAL FACTORY, INC., Naruto (JP)

( * ) Notice: Subject to any disclaimer, the term of this patent is extended or adjusted under 35 U.S.C. 154(b) by 85 days.

(21) Appl. No.: 15/254,655

(22) Filed: Sep. 1, 2016

(65) Prior Publication Data

US 2016/0367584 A1 Dec. 22, 2016

Related U.S. Application Data

(62) Division of application No. 14/360,070, filed as application No. PCT/JP2012/083039 on Nov. 22, 2012, now abandoned.

(30) Foreign Application Priority Data

Nov. 24, 2011 (JP) .................................. 2011-256516

(51) Int. Cl.
*A61K 31/7032* (2006.01)
*A61K 9/00* (2006.01)
*A61K 9/08* (2006.01)

(52) U.S. Cl.
CPC ........ *A61K 31/7032* (2013.01); *A61K 9/0048* (2013.01); *A61K 9/08* (2013.01)

(58) Field of Classification Search
CPC ............................... A61K 9/08; A61K 9/0048
USPC .......................................................... 514/25
See application file for complete search history.

(56) References Cited

U.S. PATENT DOCUMENTS

| | | | |
|---|---|---|---|
| 2005/0234011 A1 | 10/2005 | Mazzone et al. | |
| 2009/0318372 A1 | 12/2009 | Godl et al. | |
| 2010/0297034 A1 | 11/2010 | Schmittmann | |
| 2011/0053896 A1 | 3/2011 | Krutmann et al. | |
| 2011/0207681 A1 | 8/2011 | Klein et al. | |
| 2011/0306568 A1* | 12/2011 | Schwarz | A01N 43/16 |
| | | | 514/25 |

FOREIGN PATENT DOCUMENTS

| | | | | |
|---|---|---|---|---|
| EP | 1884234 A1 * | 5/2006 | ........... | A61K 31/096 |
| EP | 1 884 234 A1 | 2/2008 | | |
| JP | 05-271079 A | 10/1993 | | |
| JP | 2004-99472 A | 4/2004 | | |
| JP | 2004-331579 A | 11/2004 | | |
| JP | 2004-331581 A | 11/2004 | | |
| JP | 2005-529906 A | 10/2005 | | |
| JP | 2007-137862 A | 6/2007 | | |
| JP | 2007137862 A * | 6/2007 | ......... | A61K 31/7032 |
| JP | 2008-34158 A | 3/2008 | | |
| JP | 2010-83829 A | 4/2010 | | |
| RU | 2 406 499 C2 | 12/2010 | | |
| WO | WO 2010/049136 A2 * | 5/2010 | ............. | A01N 43/16 |

OTHER PUBLICATIONS

Dartt, , D. A., The Ocular Surface, 2004, 2(2), 76-91.*
Extended European Search Report, dated May 21, 2015, for corresponding European Application No. 12851333.0-1453 / 2783689, 6 pages.
First Examination Report, dated Mar. 12, 2015, for corresponding New Zealand Application No. 625350, 2 pages.
International Search Report, dated Jan. 22, 2013, for International Application No. PCT/JP2012/080391, 7 pages.
Japanese Office Action, dated Jan. 5, 2016, for Japanese Application No. 2013-545975, 8 pages. (with English Translation).
Lee, "Management of dry eye syndrome," Medicine Today 3(5):87-90, 2002.
Official Action, dated Oct. 18, 2016, for corresponding Russian Application No. 2014125426/15(041368), 7 pages. (with English Translation).
Russian Office Action; Application No. 2014125426, dated Feb. 14, 2017 (with English Translation) 8 pages.
J Allergy Clin Immunol. Jan. 2005; 115(1): 118-122, abstract.
"Guideline from BVA and DOG, Dry eye", Guideline No. 11, Mar. 8, 2019, 30 pages. (With English Translation).
Brockhaus, "The Encyclopedia; in twenty four bands, Twentieth, revised and updated edition" Third Volume, BED-ROM, Leipzig; Mannheim, 1996, pp. 345. (With English Machine Translation) (7 pages).

(Continued)

*Primary Examiner* — Ganapathy Krishnan

(74) *Attorney, Agent, or Firm* — Seed IP Law Group LLP

(57) ABSTRACT

An object of the present invention is to provide a protective agent for the keratoconjunctiva or a suppressive agent for a keratoconjunctival disorder having an excellent suppressive effect on a keratoconjunctival disorder. The invention relates to a protective agent for the keratoconjunctiva or a suppressive agent for a keratoconjunctival disorder containing glucosylglycerol as an active ingredient, use of glucosylglycerol for the manufacture of a pharmaceutical for protecting a keratoconjunctiva or suppressing a keratoconjunctival disorder and a method of protecting a keratoconjunctiva or suppressing a keratoconjunctival disorder comprising administering glucosylglycerol.

4 Claims, 1 Drawing Sheet

(56) References Cited

OTHER PUBLICATIONS

European Communication of a Notice of Opposition, dated Jul. 1, 2020, for the corresponding European Patent Application No. 12851333.0 (European Patent No. 2 783 689), 28 pages. (With English Translation).
Wikipedia Article, "Dry eye syndrome", last modified Sep. 14, 2020, found at URL: https://en.wikipedia.org/wiki/Dry_eye_syndrome, downloaded Oct. 2, 2020, 9 pages.

* cited by examiner

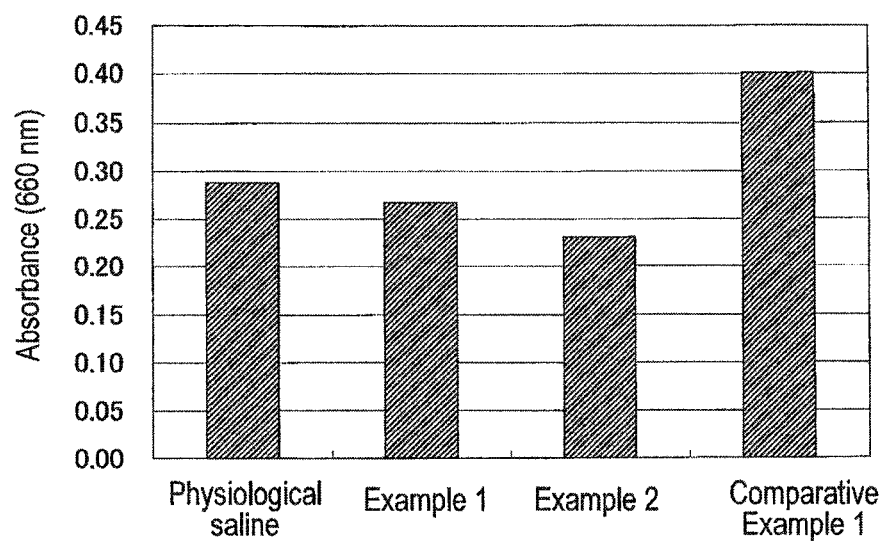

PROTECTIVE AGENT FOR KERATOCONJUNCTIVA OR SUPPRESSIVE AGENT FOR KERATOCONJUNCTIVAL DISORDER

TECHNICAL FIELD

The present invention relates to a protective agent for the keratoconjunctiva or a suppressive agent for a keratoconjunctival disorder, and more particularly relates to a protective agent for the keratoconjunctiva or a suppressive agent for a keratoconjunctival disorder, which suppresses a keratoconjunctival disorder caused by drying or the like and protects the keratoconjunctiva.

BACKGROUND ART

The lacrimal fluid is spread across the surface of the eye made up of the cornea and the conjunctiva (keratoconjunctiva) so as to keep the eye wet and prevent drying of the surface of the eye. Further, the lacrimal fluid serves as a lubricant for protecting the keratoconjunctiva from stimulation by blinking and contributes to the maintenance of smoothness of the surface of the keratoconjunctiva. In addition, the lacrimal fluid has a bacteriostatic effect so as to prevent infection with bacteria, fungi, viruses, etc., and also provides the keratoconjunctiva with oxygen and various nutrients and removes carbon dioxide and metabolites.

Recently, the number of patients with dry eye (keratoconjunctival xerosis) increases, and the cause of this dry eye is considered to be a decrease in the amount of secreted lacrimal fluid. Due to the abnormality of lacrimal fluid in terms of quality and quantity, a disorder is caused in the keratoconjunctiva to cause discomfort in the eye such as dryness, pain, or red eye, infection in the eye such as conjunctivitis, or the like. If dry eye is exacerbated, the keratoconjunctiva may be damaged to reduce visual acuity in some cases.

As a treatment of dry eye, the instillation of an artificial lacrimal fluid containing a viscoelastic substance such as hyaluronic acid and a protein such as sericin is mainly performed, and for example, a protective agent for the keratoconjunctiva or an improving agent for a keratoconjunctival disorder containing a silk protein, sericin, as an active ingredient is known (see, for example, Patent Document 1).

On the other hand, glucosylglycerol (glyceryl glucoside) is a component contained in a brewed product such as a refined sake (Japanese rice wine), and has sweetness, thermal stability, low reactivity in the Maillard reaction, water-retaining properties, non-cariogenic properties, indigestible properties, etc., and also has a promoting effect on the proliferation of vascular endothelial cells, a suppressive effect on an increase in blood glucose level, an antimicrobial effect, etc., and has been used in foods, cosmetics, pharmaceuticals, and so on. For example, a whitening agent containing α-D-glucopyranosyl glycerol (α-glucosylglycerol) as an active ingredient (see, for example, Patent Document 2), an agent for accelerating the production of dermal matrix containing α-D-glucopyranosyl glycerol (α-glucosylglycerol) as an active ingredient (see, for example, Patent Document 3), and so on are known.

As described above, α-glucosylglycerol has various effects, and therefore is applied in various ways, however, the compound is used mainly as an external preparation for the skin, and the effect thereof on the keratoconjunctiva of the eye has not been known so far.

BACKGROUND ART DOCUMENT

Patent Document

Patent Document 1: JP-A-2010-83829
Patent Document 2: JP-A-2004-331581
Patent Document 3: JP-A-2004-331579

SUMMARY OF THE INVENTION

Problems That the Invention is to Solve

As described above, an eye drop which exhibits more potent effect for suppressing the symptoms has been demanded for patients who suffer from dry eye. In such a circumstance, an object of the invention is to provide a protective agent for the keratoconjunctiva or a suppressive agent for a keratoconjunctival disorder, which has an excellent effect of suppressing a keratoconjunctival disorder caused by drying or the like and protecting the keratoconjunctiva.

Means for Solving the Problems

The present inventors made intensive studies for achieving a protective agent for the keratoconjunctiva which exhibits a suppressive effect on a keratoconjunctival disorder, and as a result, they found that glyceryl glucoside exhibits an excellent suppressive effect on a keratoconjunctival disorder, and thus completed the invention.

That is, in order to achieve the above object, the invention provides the following (1) to (6).

(1) A protective agent for a keratoconjunctiva or a suppressive agent for a keratoconjunctival disorder comprising glucosylglycerol as an active ingredient.

(2) The protective agent for the keratoconjunctiva or the suppressive agent for a keratoconjunctival disorder as described in the above (1), wherein the agent is used for protecting the keratoconjunctiva against an endogenous disease of Sjogren's syndrome, Stevens-Johnson syndrome, or dry eye syndrome (dry eye) or an exogenous disease due to postsurgery, a drug, an injury, or the wearing of a contact lens or suppressing the keratoconjunctival disorder due to said diseases.

(3) Use of glucosylglycerol for the manufacture of a pharmaceutical for protecting a keratoconjunctiva or suppressing a keratoconjunctival disorder.

(4) The use as described in the above (3), wherein the protection of the keratoconjunctiva or the suppression of the a keratoconjunctival disorder is protection of the keratoconjunctiva against an endogenous disease of Sjogren's syndrome, Stevens-Johnson syndrome, or dry eye syndrome (dry eye) or an exogenous disease due to postsurgery, a drug, an injury, or the wearing of a contact lens or the suppression of the keratoconjunctival disorder due to said diseases.

(5) A method of protecting a keratoconjunctiva or suppressing a keratoconjunctival disorder comprising administering glucosylglycerol.

(6) The method as described in the above (5) for protecting the keratoconjunctiva against an endogenous disease of Sjogren's syndrome, Stevens-Johnson syndrome, or dry eye syndrome (dry eye) or an exogenous disease due to postsurgery, a drug, an injury, or the wearing of a contact lens or suppressing the keratoconjunctival disorder due to said diseases.

Advantageous Effect of the Invention

According to the invention, a protective agent for the keratoconjunctiva and a suppressive agent for a keratoconjunctival disorder which have an excellent suppressive effect on a keratoconjunctival disorder can be provided.

BRIEF DESCRIPTION OF THE DRAWINGS

FIG. 1 is a graph showing the measurement results of absorbance measured in Examples of the invention.

MODE FOR CARRYING OUT THE INVENTION

Hereinafter, the protective agent for the keratoconjunctiva and the suppressive agent for a keratoconjunctival disorder of the invention will be described in detail.

In the invention, the "protection of the keratoconjunctiva" refers to the protection of keratoconjunctival tissue from a keratoconjunctival disorder which can be caused by any of various factors. Specifically, the "protection of the keratoconjunctiva" can be roughly divided into the protection from a keratoconjunctival disorder caused by an exogenous factor and the protection from a keratoconjunctival disorder caused by an endogenous factor. Examples of the exogenous factor include an injury, a burn injury, a chemical substance, a drug, UV light, the wearing of a contact lens, a foreign substance, an eyelash, outside air drying, and infection. Further, surgical stress in the cornea such as keratorefractive surgery or cataract surgery is also included in the exogenous factor. On the other hand, examples of the endogenous factor include Sjogren's syndrome, dry eye syndrome (dry eye), and diabetic keratopathy.

Further, in the invention, the "keratoconjunctiva" refers to the cornea and the conjunctiva, and the cornea is made up of five layers including a corneal epithelial layer, a Bowman's membrane, a corneal stromal layer, a Descemet's membrane, and a corneal endothelial layer, and the conjunctiva is made up of a conjunctival epithelial layer and a lamina propria layer. Among these, the corneal epithelial layer and the conjunctival epithelial layer are located on the outermost surfaces of the cornea and the conjunctiva, respectively, and each comprises a set of epithelial cell layers in which the cells migrate one another, and is likely to be damaged by an effect from the outside. Therefore, according to a preferred embodiment of the invention, the keratoconjunctiva in the "protection of the keratoconjunctiva" refers to the keratoconjunctival epithelium (the corneal epithelium and the conjunctival epithelium).

Further, in the invention, the "suppression of a keratoconjunctival disorder" refers to the inclusion of improvement of a keratoconjunctival disorder caused by any of the above-described factors, alleviation of the symptoms, reduction of the symptoms, mitigation of the symptoms, and also treatment, healing, acceleration of healing, and so on.

The protective agent for the keratoconjunctiva and the suppressive agent for a keratoconjunctival disorder (hereinafter sometimes referred to collectively as pharmaceutical agents) of the invention comprises glucosylglycerol as an active ingredient. As the glucosylglycerol to be used as the active ingredient, 1-α-glyceryl glucoside (Formula 1), 2-α-glyceryl glucoside (Formula 2), 1-β-glyceryl glucoside (Formula 3), and 2-β-glyceryl glucoside (Formula 4), which are represented by the following formulae (1) to (4), are known, and among these compounds, one type can be used alone or a plurality of types can be used in combination.

[Chemical Formula 1]

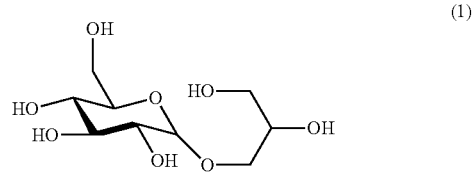
(1)

[Chemical Formula 2]

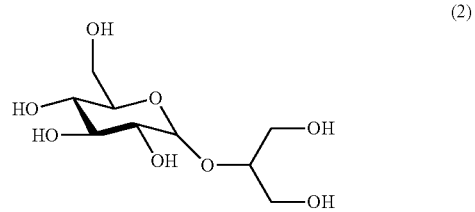
(2)

[Chemical Formula 3]

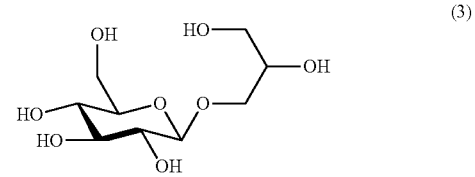
(3)

[Chemical Formula 4]

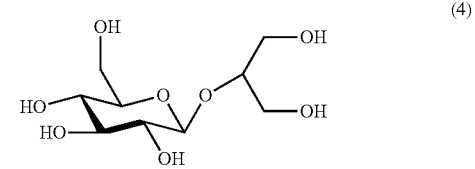
(4)

The method of obtaining such glucosylglycerol is not particularly limited, and for example, a method of allowing glycerine derived from palm to act on a substrate of a saccharide derived from corn, a method of allowing fungal α-glucosidase, cyclodextrin glucanotransferase, or sucrose phosphorylase to act on a substrate of a carbohydrate in a glycerol solution, a method of performing extraction and purification from a brewed product such as refined sake (Japanese rice wine), miso (fermented soybean paste), or mirin (sweet sake for seasoning), a method of treating isomaltose, maltitol, or the like with lead tetraacetate or a periodate to split glycol, followed by reduction, a method of subjecting β-glucoside synthesized by Koenigs-Knorr reaction to anomerization, followed by hydrolysis of β-glucoside with β-glucosidase, or the like can be used. However, a method of allowing glycerine derived from palm to act on a substrate of a carbohydrate derived from corn, a method of allowing cyclodextrin glucanotransferase to act on a substrate of a carbohydrate in a glycerol solution (see, for example, JP-A-2004-099472), or a method of allowing sucrose phosphorylase to act on a substrate of a carbohydrate in a glycerol solution (see, for example, WO 2008/034158) is particularly preferred from the viewpoint of cost and safety.

The glucosylglycerol can be used as such, but may be used after being diluted with water or a polar solvent, or after being subjected to a purification treatment of decoloring and deodorization within a range which does not cause denaturation or decomposition, or after being subjected to a fractionation treatment using column chromatography or the like. Further, the glucosylglycerol can be used after being encapsulated in a vesicle such as a liposome, a microcapsule, or the like.

The amount of the glucosylglycerol to be added to the protective agent for the keratoconjunctiva or the suppressive agent for a keratoconjunctival disorder in the invention varies depending on the dosage form or type of the pharmaceutical agent, the severity of the keratoconjunctival disorder, etc., and cannot be uniformly specified, however, for example, the glucosylglycerol is preferably contained in the pharmaceutical agent in an amount of preferably from 0.01 to 80% by mass, more preferably from 0.05 to 50% by mass, further more preferably from 0.01 to 10% by mass. If the glucosylglycerol is contained in the pharmaceutical agent in an amount of 0.01% by mass or more, the desired effect of the invention of this application is sufficiently obtained, and therefore, such an amount is preferred, and if the amount thereof is 80% by mass or less, an increase in viscosity of the pharmaceutical agent due to the glucosylglycerol falls within a desired range, and therefore, such an amount is preferred.

In the case where the protective agent for the keratoconjunctiva and the suppressive agent for a keratoconjunctival disorder of the invention are prepared as pharmaceutical preparations for ophthalmic topical administration, the pH and osmotic pressure thereof are not particularly limited as long as they fall within a range that is acceptable as a pharmaceutical preparation for ophthalmic topical administration. However, the pH thereof is preferably from 5 to 9.5, more preferably from 6 to 9, further more preferably from 7 to 9. The ratio of the osmotic pressure of the pharmaceutical preparation (except for an ophthalmic ointment) to that of physiological saline is, for example, from 0.3 to 4.3, preferably from 0.3 to 2.2, particularly preferably from about 0.5 to 1.5. The pH and osmotic pressure thereof can be adjusted by a method known in this technical field using a pH adjusting agent, an isotonizing agent, a salt, or the like.

When the protective agent for the keratoconjunctiva and the suppressive agent for a keratoconjunctival disorder of the invention are formulated into pharmaceutical preparations, various components (including a pharmacologically active component and a biologically active component) to be used in a pharmaceutical preparation for ophthalmic topical administration can be added as needed within a range that does not inhibit the effect of the invention. The type of such a component is not particularly limited, and for example, a decongestant component, an ocular accommodation agent component, an anti-inflammatory agent component or an astringent component, an antihistamine agent component or an anti-allergic agent component, a vitamin, an amino acid, an antimicrobial agent component, a microbicidal agent component, a saccharide, a polysaccharide or a derivative thereof, cellulose or a derivative thereof or a salt thereof, a water-soluble polymer other than the above-described components, a local anesthetic component, a steroid component, a therapeutic component for glaucoma, a therapeutic component for cataract, etc. can be exemplified. Among these components, one component may be used alone or two or more components may be used in combination.

Examples of the decongestant component include α-adrenergic agonists, imidazoline derivatives (such as naphazoline and tetrahydrozoline), β-phenylethylamine derivatives (such as phenylephrine, epinephrine, ephedrine, and methylephedrine), and pharmaceutically or physiologically acceptable salts thereof (for example, inorganic acid salts such as naphazoline hydrochloride, naphazoline nitrate, tetrahydrozoline hydrochloride, tetrahydrozoline nitrate, phenylephrine hydrochloride, epinephrine hydrochloride, ephedrine hydrochloride, and methylephedrine hydrochloride; organic acid salts such as epinephrine hydrogen tartrate, etc.).

Examples of the ocular muscle accommodation agent component include cholinesterase inhibitors having an active center similar to acetylcholine and quaternary ammonium compounds and salts thereof such as neostigmine methylsulfate.

Examples of the anti-inflammatory agent component or astringent component include celecoxib, rofecoxib, indomethacin, diclofenac, diclofenac sodium, piroxicam, meloxicam, aspirin, mefenamic acid, indomethacin farnesil, acemetacin, ibuprofen, tiaprofenic acid, loxoprofen sodium, tiaramide hydrochloride, epsilon-aminocaproic acid, berberine and pharmacologically acceptable salts thereof (such as berberine chloride and berberine sulfate), azulene sulfonic acid and pharmacologically acceptable salts thereof (such as azulene sulfonate sodium), zinc salts (such as zinc sulfate and zinc lactate), lysozyme, lysozyme chloride, methyl salicylate, allantoin, and glycyrrhizic acid and pharmacologically acceptable salts thereof (such as dipotassium glycyrrhizinate and ammonium glycyrrhizinate).

Examples of the antihistamine agent component or anti-allergic agent component include chlorpheniramine, diphenhydramine, iproheptine, ketotifen, emedastine, clemastine, azelastine, levocabastine, olopatadine, cromoglycic acid, tranilast, amlexanox, mequitazine, loratadine, fexofenadine, cetirizine, ibudilast, suplatast, pemirolast, repirinast, tazanolast, oxatomide, terfenadine, epinastine, astemizole, ebastine, and salts thereof (such as chlorpheniramine maleate, diphenhydramine hydrochloride, iproheptine hydrochloride, ketotifen fumarate, emedastine fumarate, clemastine fumarate, azelastine hydrochloride, levocabastine hydrochloride, olopatadine hydrochloride, and sodium cromoglicate).

Examples of the vitamin include A vitamins [such as retinal, retinol, retinoic acid, carotene, dehydroretinal, lycopene, and pharmacologically acceptable salts thereof (such as retinol acetate and retinol palmitate)], B vitamins [such as thiamine, dicethiamine, thiamine hydrochloride, thiamine nitrate, bisthiamine nitrate, thiamine disulfide, thiamine dicetyl nitrate ester salts, dicethiamine hydrochloride, fursulthiamine hydrochloride, octothiamine, cycothiamine, bisibuthiamine, bisbenthiamine, fursultiamine, prosulthiamine, benfothiamine, riboflavin, flavin adenine dinucleotide, flavin adenine dinucleotide sodium, riboflavin, riboflavin sodium phosphate, riboflavin butyrate, pyridoxine, pyridoxine hydrochloride, pyridoxal, pyridoxal phosphate, pyridoxal calcium phosphate, hydroxocobalamin hydrochloride, hydroxocobalamin acetate, cyanocobalamin, hydroxocobalamin, methylcobalamin, deoxyadenocobalamin, folic acid, tetrahydrofolic acid, dihydrofolic acid, nicotinic acid, nicotinic-acid amide, nicotinic alcohol, panthenol, pantothenic acid, calcium pantothenate, sodium pantothenate, biotin, choline, and inositol], C vitamins [such as ascorbic acid and derivatives thereof, erythorbic acid and derivatives thereof, and pharmacologically acceptable salts thereof (such as sodium ascorbate and sodium erythorbate)], D vitamins [such as ergocalciferol, cholecalciferol, hydroxycholecalciferol, dihydroxycholecalciferol, dihydrotachysterol, and pharmacologically acceptable salts thereof], E vitamins [such as tocopherol and derivatives thereof, ubiquinone derivatives, and pharmacologically acceptable salts thereof (such as tocopherol acetate, tocopherol nicotinate, tocopherol succinate, and tocopherol calcium succinate)], and other vitamins [such as carnitine, ferulic acid, γ-oryzanol, orotic acid, cyanocobalamin, rutin, eriocitrine, hesperidin, and pharmacologically acceptable salts thereof (such as carnitine chloride).

Examples of the amino acids include leucine, isoleucine, valine, methionine, threonine, alanine, phenylalanine, tryptophan, lysine, glycine, asparagine, aspartic acid, serine, glutamine, glutamic acid, proline, tyrosine, cysteine, histidine, ornithine, hydroxyproline, hydroxylysine, glycylglycine, aminoethylsulfonic acid (taurine), and salts thereof (such as potassium aspartate, magnesium aspartate, and cysteine hydrochloride).

Examples of the antimicrobial agent component or microbicidal agent component include sulfonamides (such as sulfamethoxazole, sulfisoxasol, sulfisomidine, and pharmacologically acceptable salts thereof (such as sodium sulfamethoxazole and sodium sulfisomidine)), acrinol, quaternary ammonium compounds (such as benzalkonium, benzethonium, cetylpyridinium, and pharmacologically acceptable salts thereof (such as benzalkonium chloride, benzethonium chloride, cetylpyridinium chloride, and cetylpyridinium bromide), alkylpolyaminoethylglycine, newquinolone agents (such as lomefloxacin, levofloxacin, ciprofloxacin, ofloxacin, norfloxacin and ciprofloxacin chloride), berberine and salts thereof (such as berberine sulfate), β-lactam antimicrobial agents (such as sulbenicillin and cefmenoxime), aminoglycoside antimicrobial agents (such as kanamycin, gentamicin, tobramycin, sisomicin, and micronomicin), tetracycline antimicrobial agents (such as oxytetracycline), macrolide antimicrobial agents (such as erythromycin), chloramphenicol antimicrobial agents (such as chloramphenicol), and polypeptide antimicrobial agents (such as colistin), and additional examples thereof include antiviral agents (such as idoxuridine, acyclovir, adenine arabinoside, ganciclovir, foscarnet, valacyclovir, trifluorothymidine, cidofovir, and carbocyclic oxetanocin G), and antifungal agents (such as pimaricin, fluconazole, itraconazole, miconazole, flucytosine, and amphotericin B).

Examples of the saccharide include monosaccharides (such as glucose), disaccharides (such as trehalose, lactose, and fructose), oligosaccharides (such as lactulose, raffinose, and pullulan), and sugar alcohols (such as mannitol, xylitol, and sorbitol).

Examples of the polysaccharide or derivative thereof include gum arabic, karaya gum, xanthan gum, carob gum, guar gum, guaiac resin, quince seed, Dammar gum, tragacanth, benzoin gum, locust bean gum, casein, agar, alginic acid, dextrin, dextran, carrageenan, gelatin, collagen, pectin, starch, polygalacturonic acid (alginic acid), chitin and derivatives thereof, chitosan and derivatives thereof, elastin, heparin, heparinoid, heparin sulfate, heparan sulfate, hyaluronic acid, chondroitin sulfate, and salts thereof (such as sodium alginate, sodium hyaluronate, and sodium chondroitin sulfate).

Examples of the cellulose or derivative thereof or salt thereof include cellulose, methyl cellulose, ethyl cellulose, hydroxyethyl cellulose, hydroxypropyl cellulose, hydroxypropylmethyl cellulose, carboxymethyl cellulose, carboxyethyl cellulose, and nitro cellulose.

Examples of the water-soluble polymer other than the above-described components include polyvinyl alcohols (completely or partially saponified compounds) and polyvinylpyrrolidone.

Examples of the local anesthetic component include lidocaine, oxybuprocaine, dibucaine, procaine, ethyl aminobenzoate, meprylcaine, mepivacaine, bupivacaine, cocaine, and salts thereof (such as lidocaine hydrochloride and oxybuprocaine hydrochloride).

Examples of the steroid component include hydrocortisone, prednisolone, cortisol, methylprednisolone, triamcinolone, paramethasone, betamethasone, and salts thereof.

Examples of the therapeutic component for glaucoma include timolol maleate, carteolol hydrochloride, betaxolol hydrochloride, latanoprost, unoprostone, dipivefrin hydrochloride, epinephrine, apraclonidine hydrochloride, pilocarpine hydrochloride, carbachol, dorzolamide hydrochloride, acetazolamide, methazolamide, and salts thereof.

Examples of the therapeutic component for cataract include pirenoxine, glutathione, salivary glands hormone, tiopronin, dihydroazapentacene disulfonate, and salts thereof (such as sodium 5,12-dihydroazapentacene disulfonate).

In the invention, in order to prepare pharmaceutical preparations in various desired forms, various components or additives are appropriately selected in a conventional manner according to the intended use or form thereof within a range that does not impair the effect of the invention, and one or more components or additives may be added in combination. As such a component or additive, for example, various additives which are generally used for the preparation of a pharmaceutical preparation for ophthalmic topical administration, a semi-solid preparation, a liquid preparation, etc., such as a carrier (such as water, an aqueous solvent, or an aqueous or oily base), a thickening agent, a surfactant, a preservative, an microbicidal agent or an antimicrobial agent, a pH adjusting agent, an isotonizing agent, a flavor or a refreshing agent, a chelating agent, and a buffer can be exemplified.

Examples of the thickening agent include polysaccharides and derivatives thereof (such as gum arabic, karaya gum, xanthan gum, carob gum, guar gum, guaiac resin, quince seed, Dammar gum, tragacanth gum, benzoin gum, locust bean gum, casein, agar, alginic acid, dextrin, dextran, carrageenan, gelatin, collagen, pectin, starch, polygalacturonic acid, chitin and derivatives thereof, chitosan and derivatives thereof, elastin, heparin, heparinoid, heparin sulfate, heparan sulfate, hyaluronic acid, and chondroitin sulfate), ceramide, cellulose derivatives (such as methyl cellulose, ethyl cellulose, hydroxyethyl cellulose, hydroxypropyl cellulose, hydroxypropylmethyl cellulose, carboxymethyl cellulose, carboxyethyl cellulose, cellulose, and nitro cellulose), polyvinyl alcohols (completely or partially saponified compounds), polyvinylpyrrolidone, macrogol, polyvinyl methacrylate, polyacrylic acid, carboxyvinyl polymers, polyethyleneimine, polyethylene oxide, polyethylene glycol, ribonucleic acids, deoxyribonucleic acids, methyl vinyl ether-maleic anhydride copolymers, and pharmacologically acceptable salts thereof (such as sodium alginate).

Examples of the surfactant include non-ionic surfactants such as polyoxyethylene (POE)-polyoxypropylene (POP) block copolymers, (such as poloxamer 407, poloxamer 235, and poloxamer 188), polyoxyethylene-polyoxypropylene block copolymer adducts of ethylene diamine (such as poloxamine), POE sorbitan fatty acid esters such as POE (20) sorbitan monolaurates (polysorbate 20), POE (20) sorbitan monooleates (polysorbate 80), and polysorbate 60, POE hydrogenated castor oils such as POE (60) hydrogenated castor oil, POE alkyl ethers such as POE (9) lauryl ether, POE-POP alkyl ethers such as POE (20) POP (4) cetyl ether, POE alkylphenyl ethers such as POE (10) nonylphenyl ether, and POE alkylphenyl ethers such as POE (10) nonylphenyl ether; amphoteric surfactants such as glycine surfactants such as alkyl diamino ethyl glycine, betaine acetate surfactants such as lauryl dimethyl amino acetate betaine, and imidazoline surfactants; anionic surfactants such as POE alkyl ether phosphates such as sodium POE (10) lauryl ether phosphate and salts thereof, salts of N-acylamino acid such as sodium lauroyl methyl alanine, alkyl ether carboxylate salts, N-acyltaurine salts such as sodium N-cocoylmethyltaurine, sulfonate salts such as sodium tetradecene sulfonate, alkyl sulfate salts such as sodium lauryl sulfate, POE alkyl ether sulfate salts such as sodium POE (3) lauryl ether sulfate, and α-olefin sulfonate salts; cationic surfactants such as alkyl amine salts, alkyl quaternary ammonium salts (such as benzalkonium chloride and benzethonium chloride), and alkylpyridinium salts (such as cetylpyridinium chloride and cetylpyridinium bromide).

Examples of the preservative, microbicidal agent or antimicrobial agent include sorbic acid and salts thereof (such as sorbic acid, potassium sorbate, sodium sorbate, and triclocarban sorbate), p-hydroxybenzoate esters (such as methyl p-hydroxybenzoate, ethyl p-hydroxybenzoate, propyl p-hydroxybenzoate, and butyl p-hydroxybenzoate), acrinol, methylrosaniline chloride, benzalkonium chloride, benzethonium chloride, cetylpyridinium chloride, cetylpyridinium bromide, chlorhexidine and salts thereof, polyhexamethylene biguanide, alkylpolyaminoethylglycine, benzyl alcohol, phenethyl alcohol, chlorobutanol, isopropanol, ethanol, phenoxyethanol, silver-loaded zirconium phosphate, mercurochrome, materials loaded with povidone iodine or the like, thimerosal, dehydroacetic acid, chlorxylenol, chlorophen, resorcin, orthophenyl phenol, isopropyl methylphenol, thymol, hinokitiol, sulfamine, lysozyme, lactoferrin, triclosan, 8-hydroxyquinoline, undecylenic acid, capric acid, propionic acid, benzoic acid, propionic acid, halocarban, thiabendazole, polymyxin B, 5-chloro-2-methyl-4-isothiazolin-3-one, 2-methyl-4-isothiazolin-3-one, polylysine, hydrogen peroxide, polidronium chloride, Glokill (trade name, for example, Glokill PQ, manufactured by Rhodia, Inc.), polydiallyldimethyl ammonium chloride, poly [oxyethylene(dimethyliminio)ethylene-(dimethyliminio)ethylenedichloride], polycondensation products of polyethylenepolyamine-dimethylamine epichlorohydrin (trade name: for example, Busan 1157, manufactured by Buckman Laboratories, Inc.), biguanide compounds (Cosmocil CQ (trade name, containing poly(hexamethylene biguanide) hydrochloride in an amount of about 20% by weight, manufactured by Avecia, Inc.), and pharmacologically acceptable salts thereof.

Examples of the pH adjusting agent include inorganic acids (such as hydrochloric acid, sulfuric acid, phosphoric acid, polyphosphoric acid, and boric acid), organic acids (such as lactic acid, acetic acid, citric acid, tartaric acid, malic acid, succinic acid, oxalic acid, gluconic acid, fumaric acid, propionic acid, acetic acid, aspartic acid, epsilon-aminocaproic acid, glutamic acid, and aminoethylsulfonic acid), gluconolactone, ammonium acetate, inorganic bases (such as sodium hydrogen carbonate, sodium carbonate, potassium hydroxide, sodium hydroxide, calcium hydroxide, and magnesium hydroxide), organic bases (such as monoethanolamine, triethanolamine, diisopropanolamine, triisopropanolamine, and lysine), borax, and pharmacologically acceptable salts thereof.

Examples of the isotonizing agent include inorganic salts (such as sodium chloride, potassium chloride, sodium carbonate, sodium hydrogen carbonate, calcium chloride, magnesium sulfate, sodium hydrogen phosphate, disodium hydrogen phosphate, dipotassium hydrogen phosphate, sodium thiosulphate, and sodium acetate), polyhydric alcohols (such as glycerin, propylene glycol, ethylene glycol, and 1,3-butylene glycol), and saccharides (such as glucose, mannitol, and sorbitol).

Examples of the flavor or refreshing agent include terpenes (such as menthol, camphor, borneol, geraniol, cineole, anethole, limonene, and eugenol, which may be in any form of d-, l- and dl-forms), essential oils (such as *eucalyptus* oil, bergamot oil, peppermint oil, cool mint oil, spearmint oil, fennel oil, mentha oil, cinnamon oil, and rose oil).

Examples of the chelating agent include edetic acid, citric acid, polyphosphoric acid, hexametaphosphoric acid, metaphosphoric acid, ascorbic acid, succinic acid, trihydroxymethylaminomethane, nitrilotriacetic acid, 1-hydroxyethane-1,1-diphosphonic acid, and pharmacologically acceptable salts thereof.

Examples of the buffer include borate buffers, phosphate buffers, carbonate buffers, citrate buffers, acetate buffers, epsilon-aminocaproic acid, and aspartate salts. Specific examples thereof include boric acid and salts thereof (such as sodium borate, potassium tetraborate, and potassium metaborate), phosphoric acid and salts thereof (such as sodium hydrogen phosphate, sodium dihydrogen phosphate, and potassium dihydrogen phosphate), carbonic acid and salts thereof (such as sodium hydrogen carbonate and sodium carbonate), and citric acid and salts thereof (such as sodium citrate and potassium citrate).

As for a method of producing the protective agent for the keratoconjunctiva or the suppressive agent for a keratoconjunctival disorder of the invention, the production can be appropriately performed by a known method, and for example, in the case where the agent is formulated into an eye drop, an eyewash, a solution for use in wearing contact lenses, or an agent for contact lenses, glucosylglycerol and arbitrary additive components are mixed in an appropriate diluent such as distilled water or purified water, the osmotic pressure and pH of the resulting mixture is adjusted to the above-described values, and then, the mixture is subjected to an autoclaving treatment or a filtration sterilization treatment in an aseptic environment. Then, the resulting mixture is aseptically filled into a container having been washed and sterilized, whereby the production can be achieved. Further, for example, in the case where the agent is formulated into an ophthalmic ointment, in a conventionally used ophthalmic ointment base, α-glucosylglycerol and arbitrary additive components are mixed, and the preparation can be aseptically performed according to a common procedure.

The protective agent for the keratoconjunctiva and the suppressive agent for a keratoconjunctival disorder of the invention can be applied for the purpose of preventing a keratoconjunctival disorder caused by a factor, for example, an endogenous disease of Sjogren's syndrome, Stevens-Johnson syndrome, or dry eye syndrome (dry eye), an exogenous disease due to postsurgery, a drug, an injury, or the wearing of a contact lens, or the like, alleviating such a keratoconjunctival disorder, mitigating or halting the progression of such a keratoconjunctival disorder, accelerating the healing of such a keratoconjunctival disorder, etc.

A method of applying the protective agent for the keratoconjunctiva or the suppressive agent for a keratoconjunctival disorder of the invention is not particularly limited, and can be applied on a daily basis, or the suppressive agent for a keratoconjunctival disorder may be applied with arbitrary frequency after a keratoconjunctival disorder occurs. Further, the application amount may be appropriately adjusted according to the symptoms, etc., and the agent is generally instilled about 1 to 6 times a day at a dose of about 1 to 3 drops per instillation.

EXAMPLES

Hereinafter, the invention will be more specifically described with reference to Examples, however, the invention is not limited to Examples. Incidentally, the addition amount is expressed in "% by mass" unless otherwise specified.

Examples 1 to 2 and Comparative Example 1

According to the formulation shown in Table 1, a 3% glucosylglycerol solution (Example 1) and a 10% glucosylglycerol solution (Example 2) were prepared. Further, as Comparative Example 1, an aqueous solution of 0.1% sodium hyaluronate was used. Incidentally, this glucosylglycerol is a composition (trade name: COSARTE-2G, manufactured by Toyo Sugar Refining Co., Ltd.) containing 65.2% of glyceryl glucoside (α-form: 65%, β-form: 35%), 8.1% of glyceryl maltoside, 0.7% of glyceryl maltotrioside, 6.0% of glycerin, and 20.0% of water.

TABLE 1

|  | Example 1 | Example 2 | Comparative Example 1 |
|---|---|---|---|
| Glucosylglycerol (*1) | 3 | 10 | — |
| Physiological saline | 97 | 90 | — |
| Aqueous solution of 0.1% sodium hyaluronate (*2) | — | — | 100 |

(*1): COSARTE-2G (trade name, manufactured by Toyo Sugar Refining Co., Ltd.)
(*2): 0.1% Hyalein ophthalmic solution (trade name, manufactured by Santen Pharmaceutical Co., Ltd.)

<Test Method>

General anesthesia was induced with urethane in six female New Zealand white rabbits with no abnormality in eyes, and a lid speculum was placed over both eyes of each rabbit to forcibly open the eyelids. The rabbits were divided into three groups each consisting of two rabbits. At 4 hours after opening the eyelids, to each rabbit, 50 μL of physiological saline as a control was administered by instillation in the left eye, and 50 μL of each of the ophthalmic solutions of Examples 1 to 2, and Comparative Example 1 was administered by instillation in the right eye. The eyelids were kept open for an additional 3 hours thereafter, and at 7 hours after the initiation of the test (opening of the eyelids), a 2% methylene blue solution was instilled to stain a region in which a corneal epithelial disorder was caused due to the forced opening of the eyelids, and then, the eyes were rinsed with physiological saline. After the rabbits were killed under anesthesia, the cornea was excised and extraction was performed overnight with 2 mL of an extraction solution (acetone/an aqueous solution of saturated sodium sulfate=7/3 (vol/vol)). On the next day, an absorbance at a wavelength of 660 nm was measured. The same treatment was performed for the case of physiological saline. An average value of the absorbance in each group is shown in FIG. 1. Incidentally, as for the case of physiological saline, an average value for 6 rabbits is shown.

FIG. 1 shows an absorbance at a wavelength of 660 nm, and a higher value indicates a higher severity of the keratoconjunctival disorder. As apparent from FIG. 1, it was found that the ophthalmic solutions of Examples 1 to 2 can significantly alleviate the keratoconjunctival disorder as compared with the ophthalmic solution of Comparative Example 1. Further, even as compared with physiological saline, the ophthalmic solutions of Examples 1 to 2 can alleviate the keratoconjunctival disorder, and further, as compared with the ophthalmic solution of Example 1, the ophthalmic solution of Example 2 has a higher effect of alleviating a keratoconjunctival disorder, and therefore, it was found that as the concentration of glucosylglycerol is increased, a higher effect can be obtained.

While the present invention has been described in detail with reference to specific embodiments, it is obvious to those skilled in the art that various changes and modifications can be added without departing from the spirit and scope of the present invention. The present application is based on Japanese Patent Application No. 2011-256516 filed on Nov. 24, 2011, the contents of which are incorporated herein by reference.

INDUSTRIAL APPLICABILITY

Since the protective agent for the keratoconjunctiva and the suppressive agent for a keratoconjunctival disorder of the invention have an excellent effect of alleviating a keratoconjunctival disorder, and therefore are useful as a protective agent for the keratoconjunctiva and a suppressive agent for a keratoconjunctival disorder for suppressing a keratoconjunctival disorder caused by drying or the like and protecting the keratoconjunctiva.

The invention claimed is:

1. A method of protecting keratoconjunctiva from dry eye in a subject, the method comprising: administering to the subject's eye an ophthalmic formulation comprising an effective amount of glucosylglycerol and an ophthalmically acceptable carrier, wherein the glucosylglycerol is present in an amount of from 0.01 to 10% by mass of the ophthalmic formulation.

2. The method of claim 1 wherein the glucosylglycerol is 1-α-glyceryl glucoside, 2-α-glyceryl glucoside, 1-β-glyceryl glucoside, 2-β-glyceryl glucoside or a mixture thereof.

3. A method for treating dry eye in a subject, the method comprising: administering to the subject's eye an ophthalmic formulation comprising an effective amount of glucosylglycerol and an ophthalmically acceptable carrier, wherein the glucosylglycerol is present in an amount of from 0.01 to 10% by mass of the ophthalmic formulation.

4. The method of claim 3 wherein the glucosylglycerol is 1-α-glyceryl glucoside, 2-α-glyceryl glucoside, 1-β-glyceryl glucoside, 2-β-glyceryl glucoside or a mixture thereof.

* * * * *

UNITED STATES PATENT AND TRADEMARK OFFICE
CERTIFICATE OF CORRECTION

| | |
|---|---|
| PATENT NO. | : 12,005,070 B2 |
| APPLICATION NO. | : 15/254655 |
| DATED | : June 11, 2024 |
| INVENTOR(S) | : Kyo Aizawa et al. |

It is certified that error appears in the above-identified patent and that said Letters Patent is hereby corrected as shown below:

On the Title Page

Item (62) Related U.S. Application Data:
"(62) Division of application No. 14/360,070, filed as application No. PCT/JP2012/083039 on Nov. 22, 2012, now abandoned."
Should read:
--(62) Division of application No. 14/360,070, filed as application No. PCT/JP2012/08039 on Nov. 22, 2012, now abandoned.--

Signed and Sealed this
Sixth Day of August, 2024

Katherine Kelly Vidal
*Director of the United States Patent and Trademark Office*